(12) United States Patent
Sugiyama (10) Patent No.: US 9,770,314 B2
(45) Date of Patent: Sep. 26, 2017

(54) PROSTHODONTIC DEVICE WITH DETACHABLE SUPRASTRUCTURE AND RELATED SCREW

(71) Applicant: Main Brilliant Co. Ltd., Taipei (TW)

(72) Inventor: Takahico Sugiyama, Taipei (TW)

(73) Assignee: Main Brilliant Co. Ltd., Taipei (TW)

( * ) Notice: Subject to any disclaimer, the term of this patent is extended or adjusted under 35 U.S.C. 154(b) by 85 days.

(21) Appl. No.: 14/939,783

(22) Filed: Nov. 12, 2015

(65) Prior Publication Data

US 2016/0128808 A1  May 12, 2016

(30) Foreign Application Priority Data

Nov. 12, 2014  (TW) .................................. 103139160
Sep. 18, 2015  (JP) .................................. 2015-186007

(51) Int. Cl.
*A61C 13/277*  (2006.01)
*A61C 8/00*  (2006.01)

(52) U.S. Cl.
CPC .......... *A61C 13/277* (2013.01); *A61C 8/0048* (2013.01)

(58) Field of Classification Search
CPC ............................ A61C 13/277; A61C 8/0048
See application file for complete search history.

(56) References Cited

U.S. PATENT DOCUMENTS 2,644,231 A * 7/1953 Brennan .................. A61C 5/80
433/173
3,717,931 A * 2/1973 Konig .................. A61C 13/277
433/177

(Continued)

FOREIGN PATENT DOCUMENTS

DE    4201262 A1    7/1993
DE   19956424 A1    6/2001

(Continued)

OTHER PUBLICATIONS

Extended European Search Report for European Application No. 15194265.3, dated Mar. 16, 2016.

(Continued)

*Primary Examiner* — Eduardo C Robert
*Assistant Examiner* — Hao D Mai
(74) *Attorney, Agent, or Firm* — Birch, Stewart, Kolasch & Birch, LLP (57) ABSTRACT

A detachable prosthodontic device includes an abutment, a suprastructure, and a screw. The abutment includes a hollow chamber. A screw hole is arranged on an abutment wall of the hollow chamber. The suprastructure is provided with a receiving region and an inner surface surrounding the receiving region. The screw includes a screw head and a screw rod. The screw head includes a contact member and a guiding member. When the screw is mounted in the screw hole, a portion of the screw head protrudes outward from an outer surface of the hollow chamber. When the suprastructure is sleeved onto the abutment, partial area of the outer surface of the hollow chamber contacts with partial area of the inner surface of the suprastructure, and the screw head supports an opposing side of the inner surface to apply a force onto the inner surface to thereby retain the suprastructure onto the abutment.

10 Claims, 8 Drawing Sheets

(56) References Cited

U.S. PATENT DOCUMENTS

| | | | |
|---|---|---|---|
| 4,085,506 A * | 4/1978 | Lew | A61C 8/0048 433/172 |
| 4,318,696 A * | 3/1982 | Kasama | A61C 8/0086 433/169 |
| 4,380,434 A * | 4/1983 | Weissman | A61C 13/277 433/177 |
| 4,681,542 A | 7/1987 | Baum | |
| 5,033,962 A * | 7/1991 | Scatena | A61C 8/005 433/169 |
| 5,035,619 A * | 7/1991 | Daftary | A61C 8/005 433/173 |
| 5,073,111 A * | 12/1991 | Daftary | A61C 8/005 433/173 |
| 5,106,299 A * | 4/1992 | Ghalili | A61C 8/0048 433/172 |
| 5,275,560 A | 1/1994 | Obersat | |
| 5,297,963 A * | 3/1994 | Dafatry | A61C 8/0048 433/172 |
| 5,350,302 A * | 9/1994 | Marlin | A61C 8/0048 433/173 |
| 5,431,567 A * | 7/1995 | Daftary | A61C 8/0048 433/172 |
| 5,527,182 A * | 6/1996 | Willoughby | A61C 8/0001 433/172 |
| 5,564,928 A * | 10/1996 | Gittleman | A61C 3/16 433/148 |
| 5,660,545 A * | 8/1997 | Bailey | A61C 8/005 433/173 |
| 5,667,384 A * | 9/1997 | Sutter | A61C 8/0048 433/172 |
| 5,803,735 A * | 9/1998 | Gittleman | A61C 3/16 433/172 |
| 5,842,864 A * | 12/1998 | Unger | A61C 13/273 433/172 |
| 5,873,721 A * | 2/1999 | Willoughby | A61C 8/0001 433/172 |
| 5,897,320 A * | 4/1999 | Gittleman | A61C 3/16 433/172 |
| 5,915,968 A * | 6/1999 | Kirsch | A61C 8/0018 433/169 |
| 6,227,856 B1 * | 5/2001 | Beaty | A61C 8/0001 433/172 |
| 6,250,922 B1 * | 6/2001 | Bassett | A61C 8/005 433/172 |
| 6,283,753 B1 | 9/2001 | Willoughby | |
| 6,431,866 B2 * | 8/2002 | Hurson | A61C 8/005 433/172 |
| 6,986,660 B2 * | 1/2006 | Kumar | A61C 8/005 433/173 |
| 7,066,736 B2 * | 6/2006 | Kumar | A61C 8/0001 433/172 |
| 8,992,220 B2 * | 3/2015 | Berger | A61C 8/0048 433/173 |
| 9,072,567 B2 * | 7/2015 | Benzon | A61C 8/0053 |
| 2005/0053894 A1 * | 3/2005 | Wu | A61C 8/005 433/18 |
| 2005/0074725 A1 * | 4/2005 | Wu | A61C 13/26 433/223 |
| 2006/0223029 A1 * | 10/2006 | Berger | A61C 13/275 433/172 |
| 2007/0111162 A1 * | 5/2007 | Laux | A61C 8/0048 433/173 |
| 2011/0020766 A1 | 1/2011 | Sanchez et al. | |
| 2012/0107772 A1 | 5/2012 | Lin | |
| 2012/0202173 A1 | 8/2012 | Seo et al. | |
| 2013/0224686 A1 | 8/2013 | Seo | |

FOREIGN PATENT DOCUMENTS

| | | |
|---|---|---|
| DE | 20004572 U1 | 8/2001 |
| EP | 0923909 A1 | 6/1999 |
| JP | 2009-527339 A | 7/2009 |
| JP | 2012-532734 A | 12/2012 |
| KR | 10-1253498 B1 | 4/2013 |
| KR | 10-2014-0008252 A | 1/2014 |
| TW | M468295 U | 12/2013 |
| WO | WO 02/24104 A1 | 3/2002 |
| WO | WO 2007/100966 A1 | 9/2007 |
| WO | WO 2011/008605 A1 | 1/2011 |
| WO | WO 2014/064117 A2 | 5/2014 |

OTHER PUBLICATIONS

Singaporean Search Report and Written Opinion for Singaporean Application No. 10201509345P, dated May 5, 2016.

Japanese Office Action for Japanese Application No. 2015-186007, dated Jun. 21, 2016, with an English translation.

Singaporean Written Opinion dated Mar. 15, 2017 for Singapore Application No. 10201509345P.

* cited by examiner

PROSTHODONTIC DEVICE WITH DETACHABLE SUPRASTRUCTURE AND RELATED SCREW

CROSS-REFERENCE TO RELATED APPLICATIONS

This application claims the benefit of priority to Patent Application No. 103139160, filed in Taiwan on Nov. 12, 2014; the entirety of which is incorporated herein by reference for all purposes.

This application claims the benefit of priority to Patent Application No. 2015-186007, filed in Japan on Sep. 18, 2015; the entirety of which is incorporated herein by reference for all purposes.

BACKGROUND

The disclosure generally relates to a prosthodontic device and, more particularly, to a prosthodontic device with detachable suprastructure and a related screw.

For esthetic reasons or oral healthy concerns, many people opt to replace the damaged tooth with an artificial tooth through a dental implant treatment. The traditional dental implant treatment utilizes an adhesive to fill the gap between the suprastructure and the abutment so as to secure the suprastructure onto the abutment.

However, once the adhesive is cured, it is very difficult to apart the suprastructure from the abutment. As a result, periodontal disease may easily occurs because due to the difficulty of cleaning the lower portion around the artificial tooth, thereby reducing the lifetime of the artificial tooth. If the dentist or dental technician applies too much force to forcedly separate the suprastructure from the abutment, it may damage the structure or appearance of the suprastructure or the structure of the abutment.

SUMMARY

An example embodiment of a detachable prosthodontic device is disclosed, comprising: an abutment for connecting with an implant and comprising an abutment collar and a hollow chamber, wherein the hollow chamber comprises an opening and an outer surface, and a screw hole is arranged on the abutment wall of the hollow chamber; a suprastructure provided with a receiving region and an inner surface surrounding the receiving region; and a screw comprising a screw head and a screw rod, wherein the screw head comprises a contact member and a guiding member, the screw rod is provided with a screw thread, the contact member comprises a top surface, the guiding member is positioned between the contact member and the screw rod, and when the screw is mounted in the screw hole, a portion of the screw head protrudes outward from the outer surface of the hollow chamber but the screw does not penetrates the suprastructure; wherein when the suprastructure is sleeved onto the abutment, partial area of the outer surface of the hollow chamber contacts with partial area of the inner surface of the suprastructure, and the screw head supports an opposing side of the inner surface to apply a force onto the inner surface to thereby detachably retain the suprastructure onto the abutment.

Another example embodiment of a screw for use in a detachable prosthodontic device is disclosed. The detachable prosthodontic device comprises an abutment and a suprastructure, wherein the abutment is utilized for connecting with an implant and comprises an abutment collar and a hollow chamber, the hollow chamber comprises an opening and an outer surface, a screw hole is arranged on the abutment wall of the hollow chamber, and the suprastructure is provided with a receiving region and an inner surface surrounding the receiving region. The screw comprises: a screw head comprising a contact member and a guiding member; and a screw rod provided with a screw thread; wherein the contact member comprises a top surface, the guiding member is positioned between the contact member and the screw rod, and when the screw is mounted in the screw hole, a portion of the screw head protrudes outward from the outer surface of the hollow chamber but the screw does not penetrate the suprastructure; wherein when the suprastructure is sleeved onto the abutment, partial area of the outer surface of the hollow chamber contacts with partial area of the inner surface of the suprastructure, and the screw head supports an opposing side of the inner surface to apply a force onto the inner surface to thereby detachably retain the suprastructure onto the abutment.

Both the foregoing general description and the following detailed description are examples and explanatory only, and are not restrictive of the invention as claimed.

DETAILED DESCRIPTION

Reference is made in detail to embodiments of the invention, which are illustrated in the accompanying drawings. The same reference numbers may be used throughout the drawings to refer to the same or like parts, components, or operations.

Figure 1:
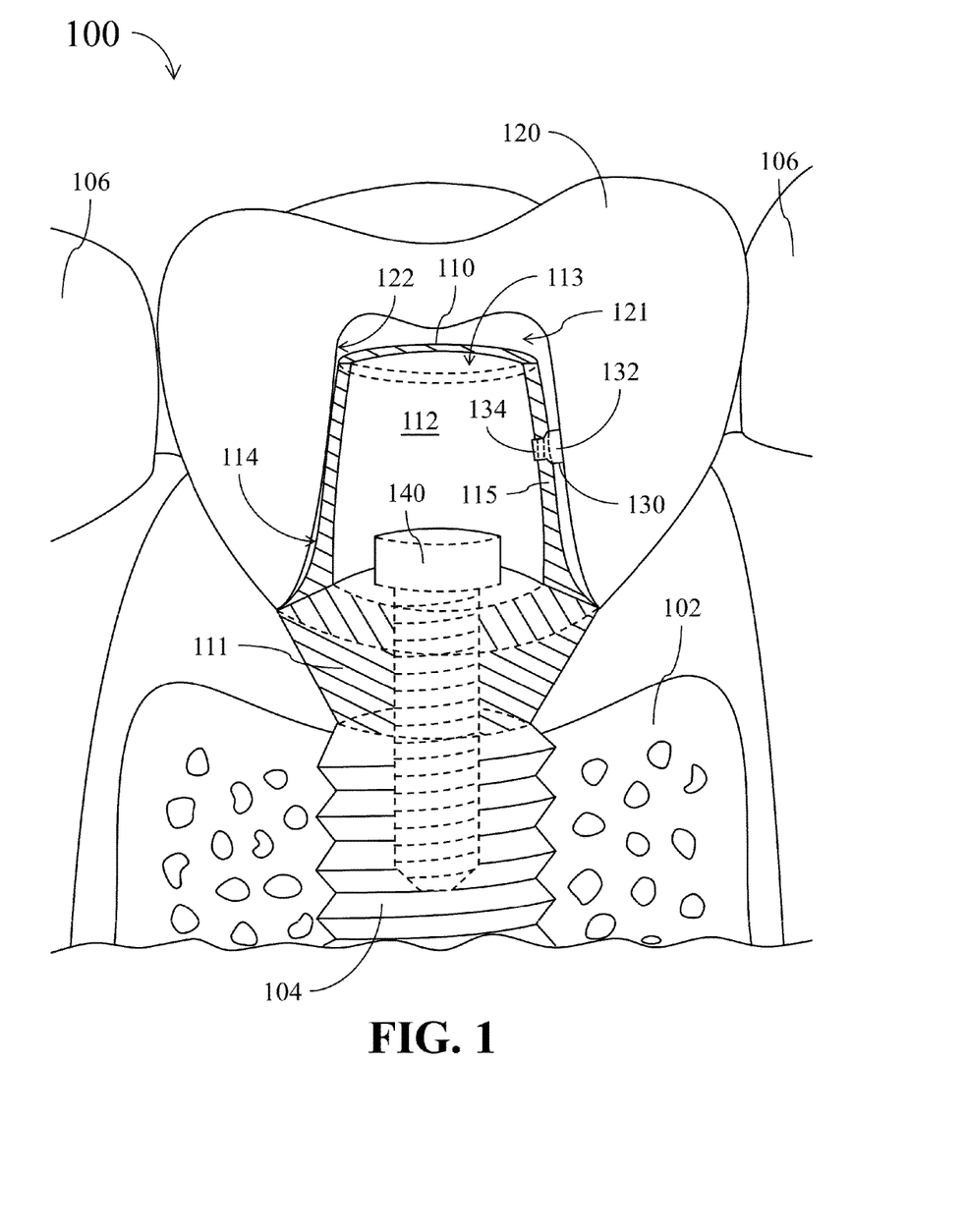
FIG. 1 shows a simplified sectional schematic diagram of a detachable prosthodontic device according to one embodiment of the present disclosure.

FIG. 1 shows a simplified sectional schematic diagram of a detachable prosthodontic device 100 according to one embodiment of the present disclosure. As shown in FIG. 1, the detachable prosthodontic device 100 comprises an abutment 110, a suprastructure 120, and a screw 130. The abutment 110 is utilized for connecting with an implant 104 implanted into the bone 102. The abutment 110 comprises an abutment collar 111 and a hollow chamber 112. The suprastructure 120 is provided with a receiving region 121 and an inner surface 122 surrounding the receiving region 121. The screw 130 comprises a screw head 132 and a screw rod 134. In this embodiment, the hollow chamber 112 of the abutment 110 comprises an opening 113 and an outer surface 114, wherein an abutment wall 115 of the hollow chamber 112 is provided with a screw hole.

As illustrated in FIG. 1, an abutment screw 140 may be put into the hollow chamber 112 through the opening 113 of the hollow chamber 112. The dentist or dental technician may press the abutment screw 140 to penetrate through the abutment collar 111 and then mount the abutment screw 140 into the implant 104, so as to secure the abutment 110 on the implant 104.

Figure 2:
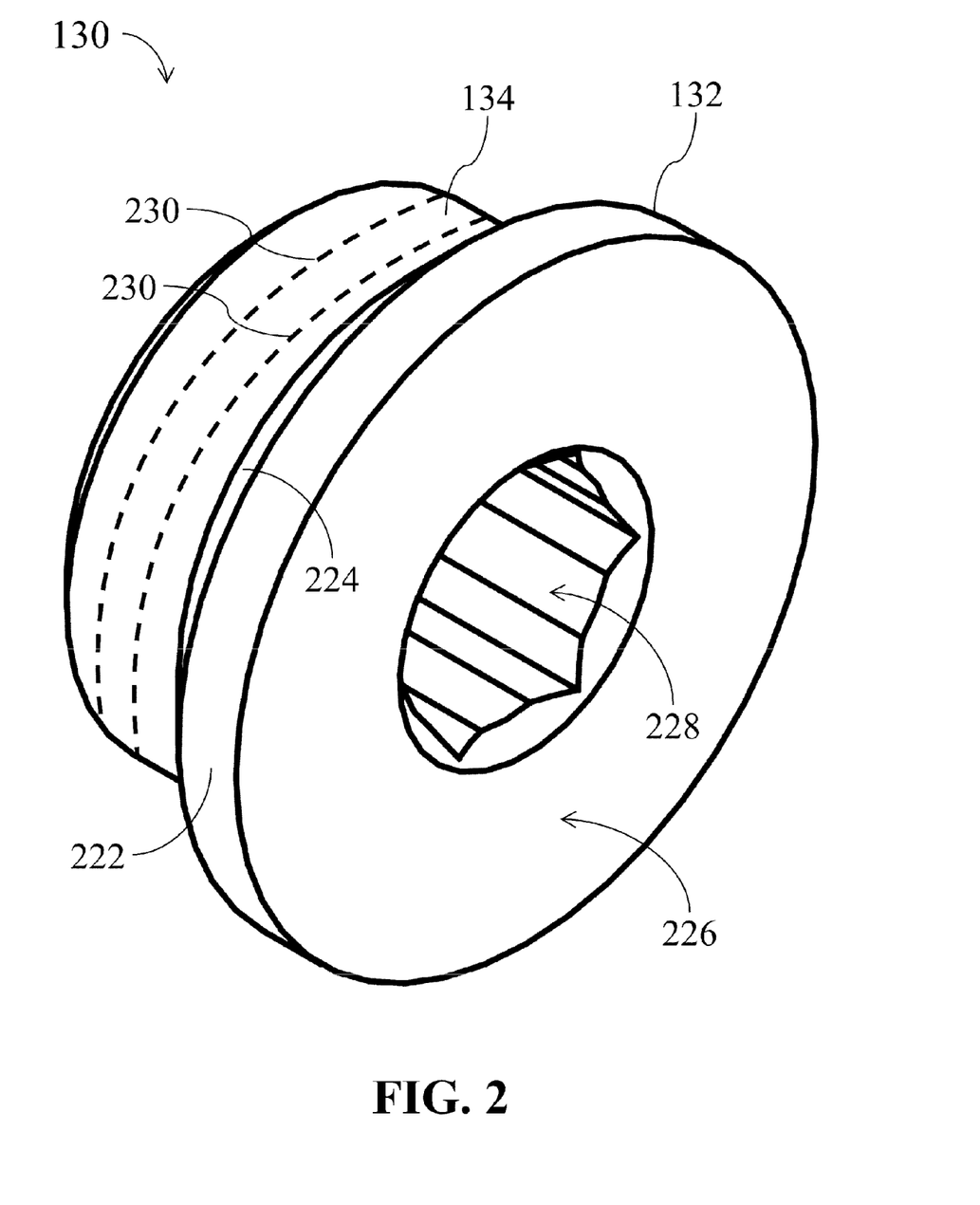
FIG. 2 shows a simplified schematic diagram of a screw in FIG. 1 according to one embodiment of the present disclosure.
Figure 3:
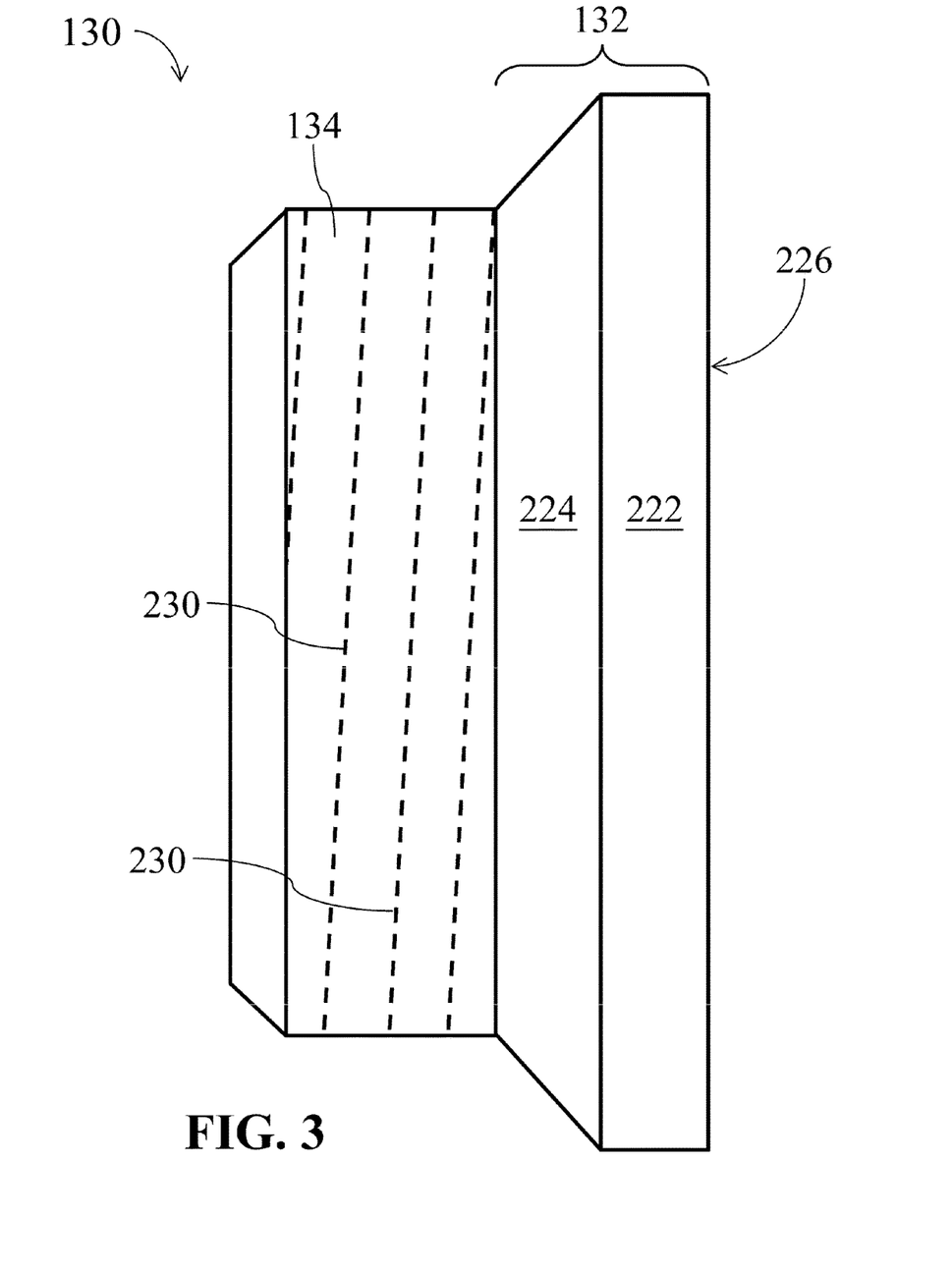
FIG. 3 shows a simplified sectional diagram of the screw in FIG. 1 according to one embodiment of the present disclosure.

An exemplary implementation of the screw 130 will be further described in the following by reference to FIGS. 2-3. FIG. 2 shows a simplified schematic diagram of the screw 130 according to one embodiment of the present disclosure. FIG. 3 shows a simplified sectional diagram of the screw 130 according to one embodiment of the present disclosure.

As shown in FIG. 2 and FIG. 3, the screw head 132 comprises a contact member 222 and a guiding member 224. The contact member 222 comprises a top surface 226. The guiding member 224 is positioned between the contact member 222 and the screw rod 134, and has a chamfer structure. The screw rod 134 is provided with a screw thread 230.

In the embodiment of FIG. 2, the contact member 222 of the screw head 132 has a rectangular-shaped lateral face. As shown in FIG. 2, the screw head 132 is further provided with a tool slot 228. In practice, the tool slot 228 may be designed to have, but not limited to, an I-shaped appearance, a cross-shaped appearance, a triangular appearance, a hexagonal appearance, or a star-shaped appearance, so that the operator can use a corresponding screwdriver or other tool to insert into the tool slot 228 and then mount the screw 130 into the screw hole on the abutment wall 115 of the hollow chamber 112. In addition, the tool slot 228 may be designed to be penetrating through the screw 130 to reduce required amount of material for implementing the screw 130.

Please refer to FIGS. 4-7, which collectively show simplified schematic diagrams illustrating a method for mounting the screw 130 onto the abutment wall 115 of the abutment 110 according to one embodiment of the present disclosure.

Figure 4:
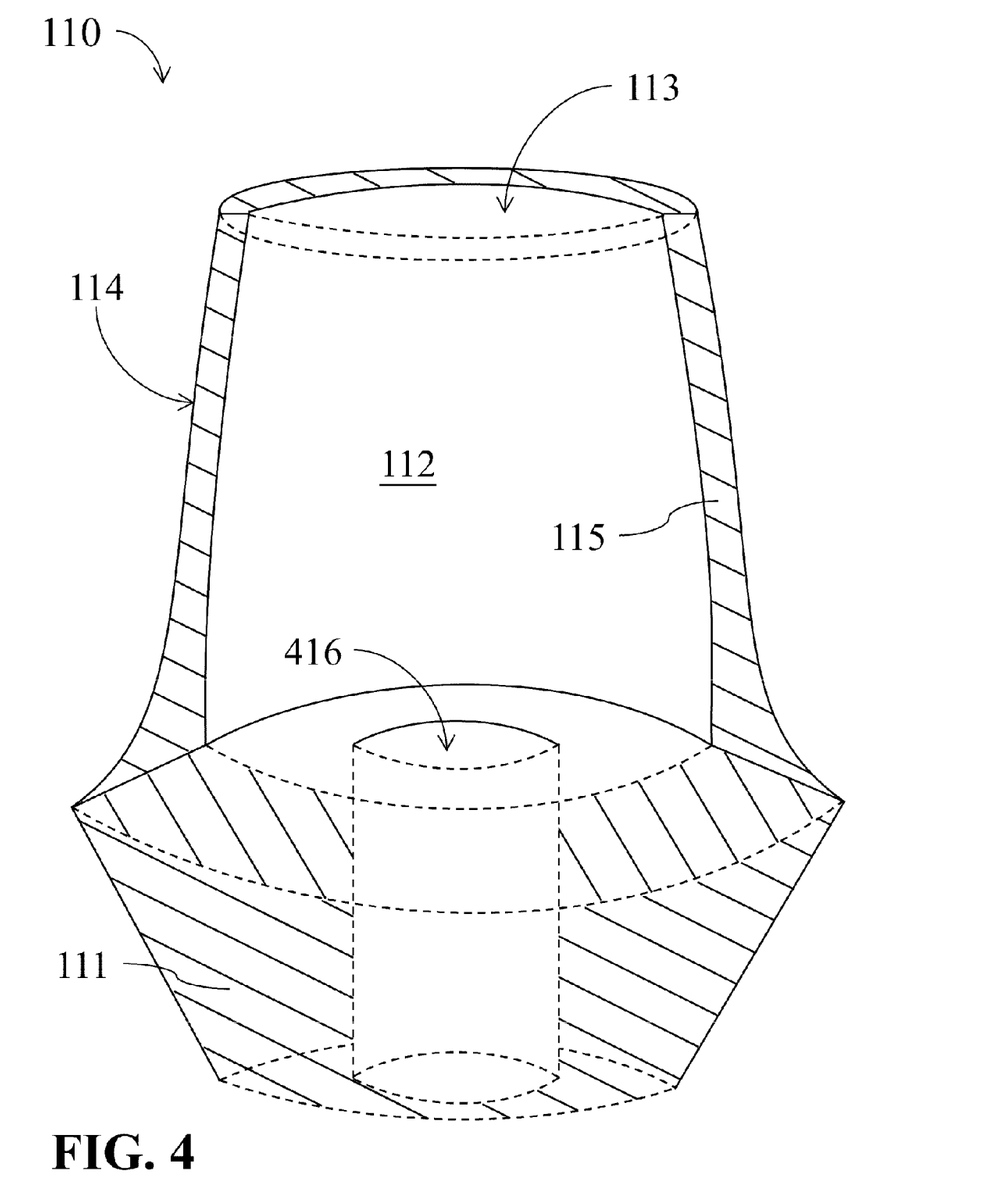
FIGS. 4~7 collectively show simplified schematic diagrams illustrating a method for mounting the screw in FIG. 1 onto an abutment according to one embodiment of the present disclosure.

FIG. 4 shows a simplified sectional schematic diagram of the abutment 110 according to one embodiment of the present disclosure. In this embodiment, the abutment collar 111 of the abutment 110 is provided with an abutment screw hole 416 penetrating through the abutment collar 111.

Figure 5:
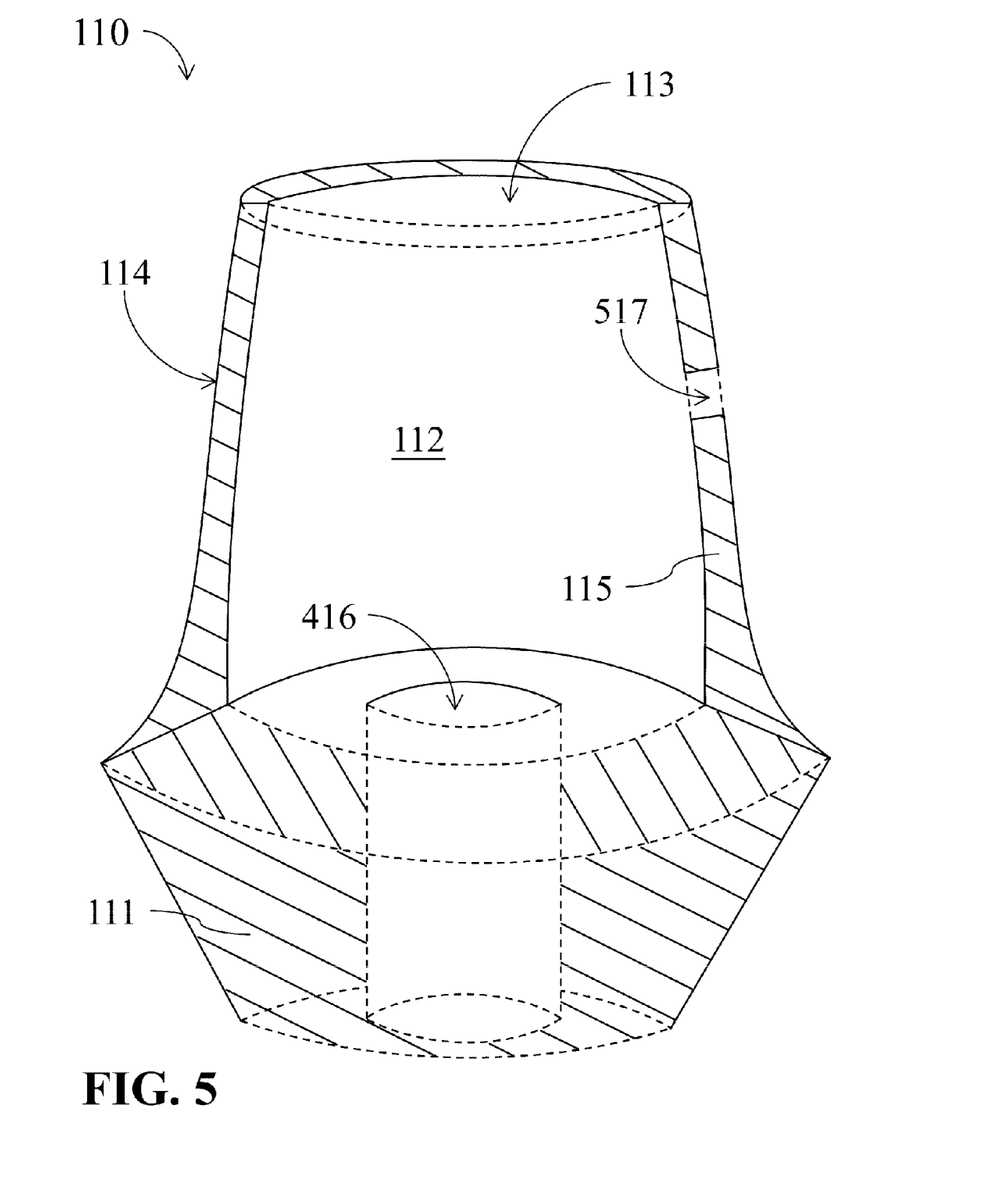

As shown in FIG. 5, before mounting the screw 130 onto the abutment wall 115 of the abutment 110, a screw hole 517 should be formed on the abutment wall 115 of the hollow chamber 112. In practice, the screw hole 517 may be designed to have a deepness corresponding to the length of the screw rod 134 of the screw 130. For example, in some embodiments, the screw hole 517 may be realized with a blind hole which does not penetrate through the abutment wall 115. In other embodiments, the screw hole 517 may be instead realized with a through hole penetrating through the abutment wall 115.

Figure 6:
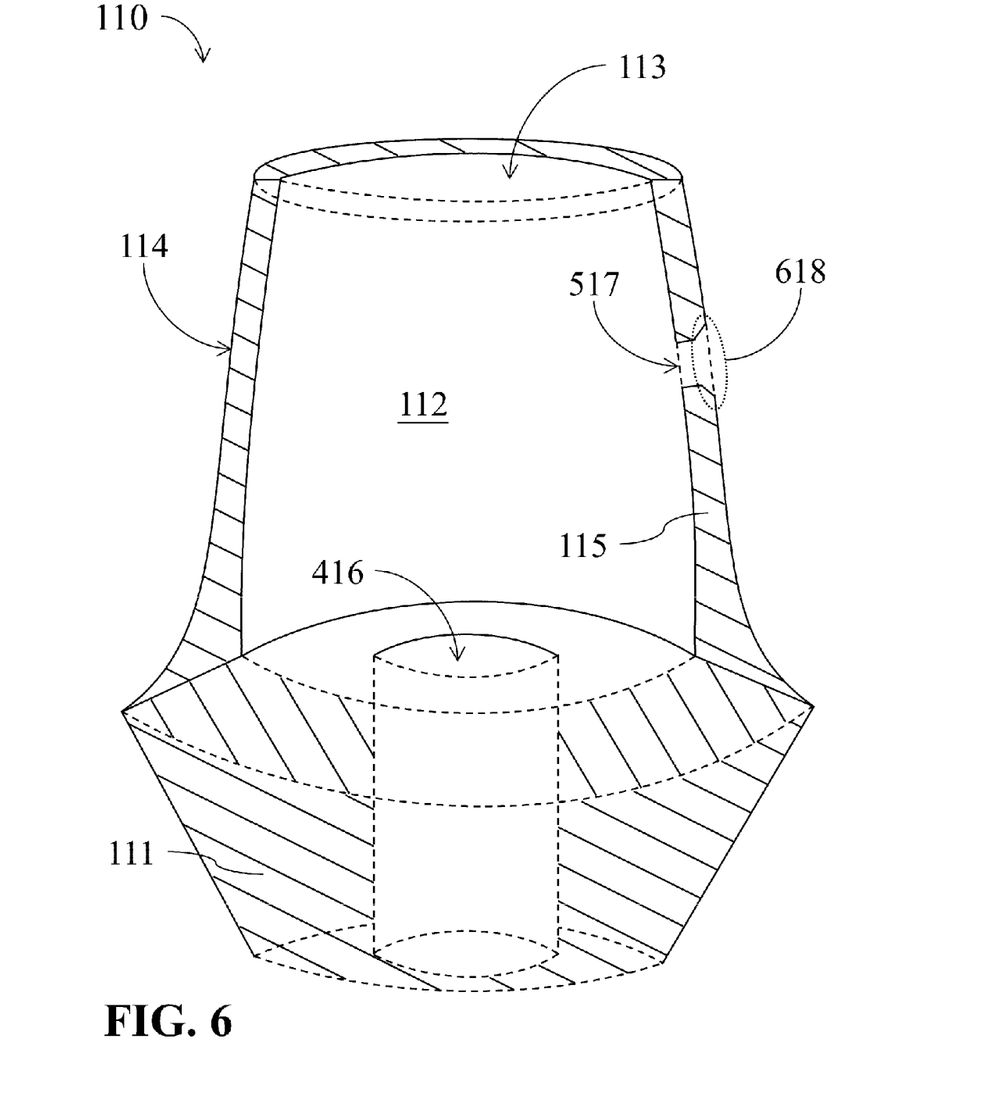

Then, as shown in FIG. 6, a guiding region 618 having a size and a shape matching with the guiding member 224 of the screw 130 is formed in the screw hole 517. For example, the guiding region 618 of this embodiment has a round shape. The guiding region 618 has a diameter identical to or slightly greater than the diameter of the guiding member 224 of the screw 130, and the diameters of the guiding region 618 and the guiding member 224 are both greater than the diameter of the screw rod 134.

When mounting the screw 130 into the screw hole 517 on the abutment wall 115, the cooperation between the chamfer structure of the guiding member 224 and the guiding region 618 enables the operator to easily and precisely mount the screw 130 into the screw hole 517, thereby avoiding the screw 130 from misalignment.

Figure 7:
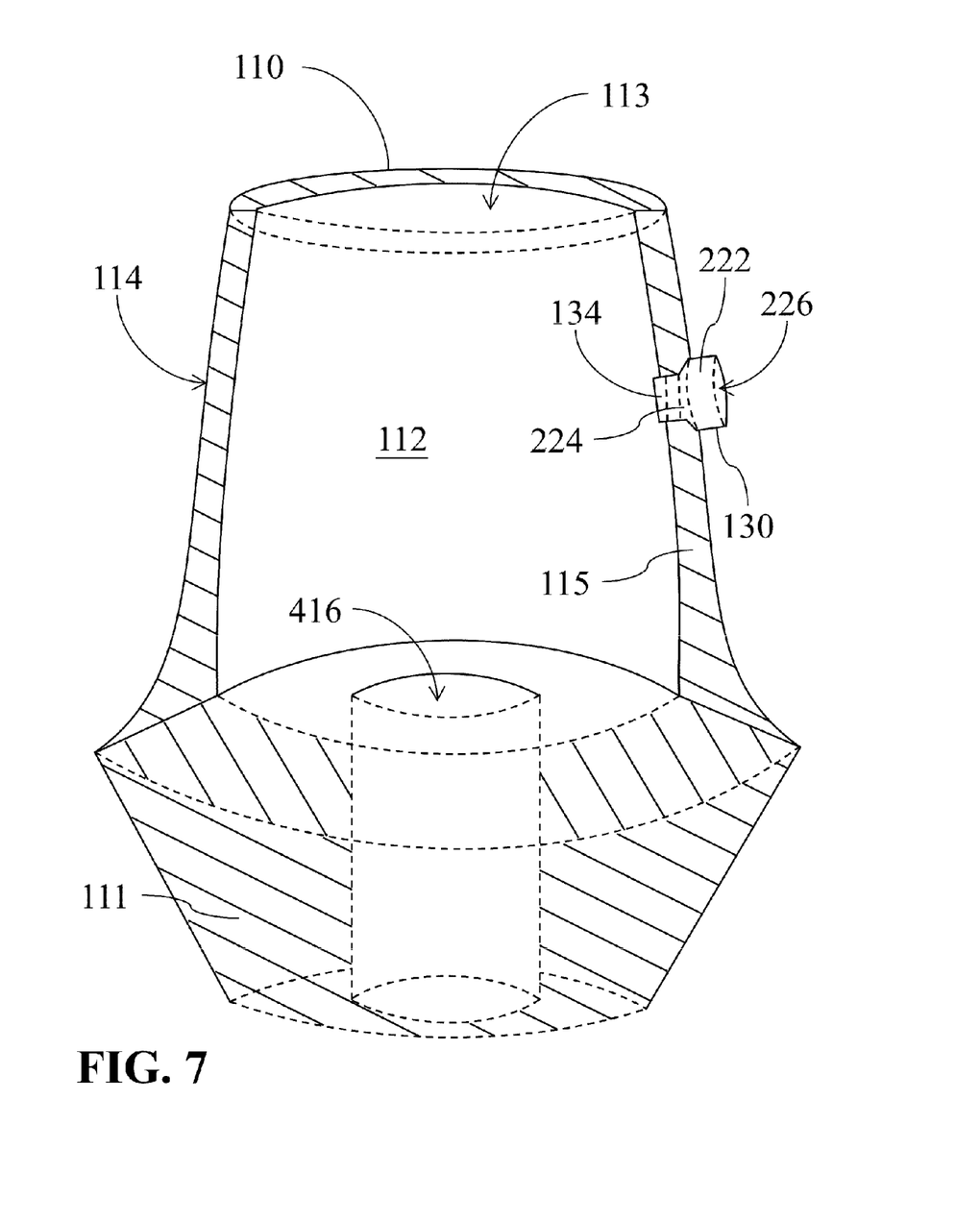

When the screw 130 is mounted in the screw hole 517, a portion of the screw head 132 protrudes outward from the outer surface 114 of the hollow chamber 112. As shown in FIG. 7, for example, when the screw 130 is mounted in the screw hole 517, the guiding member 224 is positioned within the guiding region 618, and the contact member 222 protrudes outward from the outer surface 114 of the hollow chamber 112.

When the suprastructure 120 is sleeved onto the abutment 110, partial area of the outer surface 114 of the hollow chamber 112 contacts with partial area of the inner surface 122 of the suprastructure 120, and the screw head 132 supports an opposing side of the inner surface 122 to apply a retention force to the inner surface 122 to thereby detachably retain the suprastructure 120 onto the abutment 110.

Figure 8:
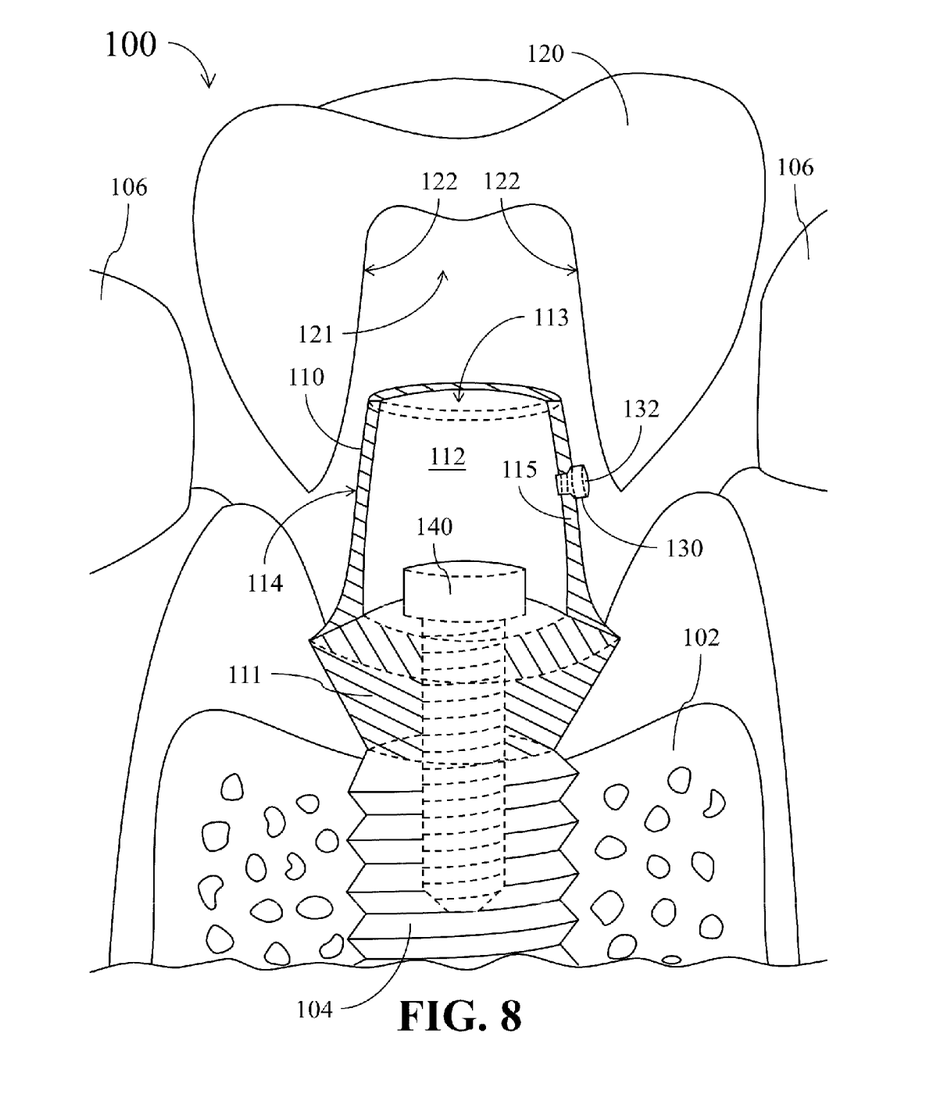
FIG. 8 shows a simplified schematic diagram illustrating a method for retaining the detachable prosthodontic device in FIG. 1 onto an implant according to one embodiment of the present disclosure.

For example, FIG. 8 shows a simplified schematic diagram illustrating a method for retaining the detachable prosthodontic device 100 onto the implant 104 according to one embodiment of the present disclosure. As described previously, the operator may put the abutment screw 140 into the hollow chamber 112 of the abutment 110 through the opening 113, press the abutment screw 140 to penetrate through the abutment screw hole 416 of the abutment collar 111, and then mount the abutment screw 140 into the implant 104. As a result, the abutment 110 can be secured on the implant 104.

Then, the operator only needs to align the receiving region 121 of the suprastructure 120 with the abutment 110 and press the suprastructure 120 toward the abutment 110 to sleeve the suprastructure 120 onto the abutment 110, then partial area of the outer surface 114 of the hollow chamber 112 would contact with partial area of the inner surface 122 of the suprastructure 120. In this situation, the contact member 222 of the screw head 132 would touch and support the opposing side of the inner surface 122 of the receiving region 121 to apply a retention force to the inner surface 122. As a result, the suprastructure 120 can be detachably retained onto the abutment 110 easily due to the friction force between the outer surface 114 of the hollow chamber 112 and the inner surface 122 of the suprastructure 120 together with the friction force between the contact member 222 of the screw head 132 and the inner surface 122 of the receiving region 121.

If it is necessary to separate the suprastructure 120 from the abutment 110 afterwards, the operator can overcome the friction force between the suprastructure 120 and the abutment 110 and the friction force between the suprastructure 120 and the screw 130 by applying appropriate force to push the suprastructure 120 to move toward the opposing direction of the abutment 110. As a result, the suprastructure 120 can be separated from the abutment 110 without damaging the structure or appearance of the suprastructure 120 and the abutment 110.

Accordingly, the disclosed method of utilizing the screw 130 to retain the suprastructure 120 onto the abutment 110 is beneficial to the cleaning, sterilization, or treatment of the tissue around the detachable prosthodontic device 100, beneficial to the cleaning or treatment of the gap between the detachable prosthodontic device 100 and adjacent tooth 106, and also beneficial to the repairing or replacement of the suprastructure 120.

Please note that when the suprastructure 120 is retained onto the abutment 110, the screw head 132 of the screw 130 merely supports the inner surface of the receiving region 121 of the suprastructure 120, but the screw 130 does not penetrate the suprastructure 120. Therefore, the screw 130 would not expose outside the suprastructure 120 and would not damage the structure and integrity of the suprastructure 120.

Additionally, it can be appreciated that not every arbitrary screw can be utilized to realize the function of the screw 130. In fact, the screw 130 requires specially designed shape and size, so that it can be applied in more occasions where different abutment and suprastructure are employed. The implementation of the screw 130 will be further elaborated in the following.

In practice, the length of the screw rod 134 of the screw 130 should be dimensioned properly in order to prevent the screw 130 from becoming an obstacle for the installation and removal of the abutment screw 140.

In some embodiments, for example, the screw rod (134) may be designed to have a length less than a half of an inner diameter of the hollow chamber 112.

In other embodiments, the screw rod 134 may be designed to have a length less than a thickness of the abutment wall 115 of the hollow chamber 112.

In some embodiments, the screw rod 134 may be designed to have a length less than 150% of the thickness of the abutment wall 115 of the hollow chamber 112.

According to the experiments, the screw 130 can support most existing abutment structures and thus have the widest application scope in the case of that the screw rod 134 is designed to have a length ranging from 0.5 to 3.5 millimeters.

Furthermore, the thread turns or the screw pitch of the screw rod 134 should be dimensioned properly so as to enhance the stability when the screw 130 is mounted in the screw hole 517 on the abutment wall 115.

According to the experiments, for example, when the thread turns of the screw rod 134 is deigned to be ranging from 1.5 to 6, the compactness between the screw 130 and the screw hole 517 can be effectively increased and thus prevent damage to the inner thread of the screw hole 517, thereby extending the lifetime of the screw 130.

In addition, the compactness between the screw 130 and the screw hole 517 can also be effectively increased and thus prevent damage to the inner thread of the screw hole 517 when the screw rod 134 is designed to have a screw pitch ranging from 0.1 to 1.0 millimeter.

In practice, the screw head 132 is preferably designed to have a diameter ranging from 0.5 to 3.0 millimeters so as to provide better retention effect.

Please note that the shape of the above-mentioned abutment 110 is merely an exemplary embodiment, rather than a restriction to the practical implementations. For example, the appearance of the abutment 110 and the shape and size of the hollow chamber 112 can be modified based on the actual requirements.

It can be appreciated from the foregoing descriptions that the operator only needs to align the receiving region 121 of the suprastructure 120 with the abutment 110 and press the suprastructure 120 toward the abutment 110 to sleeve the suprastructure 120 onto the abutment 110. In this way, the suprastructure 120 can be detachably retained onto the abutment 110 easily due to the friction force between the outer surface 114 of the hollow chamber 112 and the inner surface 122 of the suprastructure 120 together with the friction force between the contact member 222 of the screw head 132 and the inner surface 122 of the receiving region 121.

If it is necessary to separate the suprastructure 120 from the abutment 110 in the future, the operator is enabled to separate the suprastructure 120 from the abutment 110 by merely applying appropriate force to push the suprastructure 120 to move toward the opposing direction of the abutment 110, without damaging the structure or appearance of the suprastructure 120 and the abutment 110.

Accordingly, the disclosed method of utilizing the screw 130 to retain the suprastructure 120 onto the abutment 110 is beneficial to the cleaning, sterilization, or treatment of the tissue around the detachable prosthodontic device 100, beneficial to the cleaning or treatment of the gap between the detachable prosthodontic device 100 and adjacent tooth 106, and also beneficial to the repairing or replacement of the suprastructure 120.

In some of the above embodiments, the contact member 222 of the screw head 132 is designed to have a rectangular-shaped lateral face. Such appearance is a special design for offering more application flexibility to the operator, rather than a simple design choice. The operator is allowed to grind the shape of the contact member 222 based on the actual requirement, so that the resulting contact member 222 can have a shape more adaptive to the shape of the receiving region 121 of the suprastructure 120 or more adaptive to the gap between the suprastructure 120 and the abutment 110, thereby increasing the compactness between the suprastructure 120 and the abutment 110.

The structure of the disclosed screw 130 is applicable to various abutments of different structures, and thus screw 130 can be widely utilized in many applications.

Furthermore, since the screw 130 is covered by the receiving region 121 of the suprastructure 120 and doers not expose outside the suprastructure 120, the screw 130 is therefore protected by the suprastructure 120 and would not easily damaged or rusted. As a result, the lifetime of the detachable prosthodontic device 100 can be effectively increased.

Additionally, since the screw 130 does not expose outside the suprastructure 120, the screw 130 causes no adverse effect to the esthetics of the detachable prosthodontic device 100, and would not cause any uncomfortableness for the oral cavity.

Certain terms are used throughout the description and the claims to refer to particular components. One skilled in the art appreciates that a component may be referred to as different names. This disclosure does not intend to distinguish between components that differ in name but not in function. In the description and in the claims, the term "comprise" is used in an open-ended fashion, and thus should be interpreted to mean "include, but not limited to." The phrases "be coupled with," "couples with," and "coupling with" are intended to compass any indirect or direct connection. Accordingly, if this disclosure mentioned that a first device is coupled with a second device, it means that the first device may be directly or indirectly connected to the second device through electrical connections, wireless communications, optical communications, or other signal connections with/without other intermediate devices or connection means.

The term "and/or" may comprise any and all combinations of one or more of the associated listed items. In addition, the singular forms "a," "an," and "the" herein are intended to comprise the plural forms as well, unless the context clearly indicates otherwise.

Throughout the description and claims, the term "element" contains the concept of component, layer, or region.

In the drawings, the size and relative sizes of some elements may be exaggerated or simplified for clarity. Accordingly, unless the context clearly specifies, the shape, size, relative size, and relative position of each element in the drawings are illustrated merely for clarity, and not intended to be used to restrict the claim scope.

For the purpose of explanatory convenience in the specification, spatially relative terms, such as "on," "above," "below," "beneath," "higher," "lower," "upward," "downward," and the like, may be used herein to describe the function of a particular element or to describe the relationship of one element to another element(s) as illustrated in the drawings. It will be understood that the spatially relative terms are intended to encompass different orientations of the element in use, in operations, or in assembly in addition to the orientation depicted in the drawings. For example, if the element in the drawings is turned over, elements described as "on" or "above" other elements would then be oriented "under" or "beneath" the other elements. Thus, the exemplary term "beneath" can encompass both an orientation of above and beneath.

Throughout the description and claims, it will be understood that when a component is referred to as being "positioned on," "positioned above," "connected to," "engaged with," or "coupled with" another component, it can be directly on, directly connected to, or directly engaged with the other component, or intervening component may be present. In contrast, when a component is referred to as being "directly on," "directly connected to," or "directly engaged with" another component, there are no intervening components present.

Other embodiments of the invention will be apparent to those skilled in the art from consideration of the specification and practice of the invention disclosed herein. It is intended that the specification and examples be considered as exemplary only, with a true scope and spirit of the invention indicated by the following claims.

What is claimed is:

1. A detachable prosthodontic device (100), comprising:
    an abutment (110) for connecting with an implant (104) and comprising an abutment collar (111) and a hollow chamber (112), wherein the hollow chamber (112) comprises an opening (113) and an outer surface (114), and a screw hole (517) is arranged on an abutment wall (115) of the hollow chamber (112);
    a suprastructure (120) provided with a receiving region (121) and an inner surface (122) surrounding the receiving region (121); and
    a screw (130) comprising a screw head (132) and a screw rod (134), wherein the screw head (132) comprises a contact member (222) and a guiding member (224), the screw rod (134) is provided with a screw thread (230), the contact member (222) comprises a top surface (226), the guiding member (224) is positioned between the contact member (222) and the screw rod (134), and when the screw (130) is mounted in the screw hole (517), a portion of the screw head (132) protrudes outward from the outer surface (114) of the hollow chamber (112) but the screw (130) does not penetrate the suprastructure (120);
    wherein when the suprastructure (120) is sleeved onto the abutment (110), partial area of the outer surface (114) of the hollow chamber (112) contacts with partial area of the inner surface (122) of the suprastructure (120), and the screw head (132) supports an opposing side of the inner surface (122) to apply a force onto the inner surface (122) to thereby detachably retain the suprastructure (120) onto the abutment (110).

2. The detachable prosthodontic device (100) of claim 1, wherein a guiding region (618) having an shape matching with the guiding member (224) is arranged in the screw hole (517), when the screw (130) is mounted in the screw hole (517), the guiding member (224) is positioned in the guiding region (618) and the contact member (222) protrudes outward from the outer surface (114) of the hollow chamber (112), and when the partial area of the outer surface (114) of the hollow chamber (112) contacts with the partial area of the inner surface (122) of the suprastructure (120), the contact member (222) supports the opposing side of the inner surface (122) to apply the force onto the inner surface (122).

3. The detachable prosthodontic device (100) of claim 2, wherein the contact member (222) has a rectangular-shaped lateral face.

4. The detachable prosthodontic device (100) of claim 1, wherein the screw rod (134) has a length less than a half of an inner diameter of the hollow chamber (112).

5. The detachable prosthodontic device (100) of claim 1, wherein the screw rod (134) has a length less than a thickness of the abutment wall (115) of the hollow chamber (112).

6. The detachable prosthodontic device (100) of claim 1, wherein the screw rod (134) has a length less than 150% of a thickness of the abutment wall (115) of the hollow chamber (112).

7. The detachable prosthodontic device (100) of claim 1, wherein the screw rod (134) has a length ranging from 0.5 to 3.5 millimeters.

8. The detachable prosthodontic device (100) of claim 1, wherein the screw thread (230) of the screw rod (134) comprises 1.5 to 6 thread turns.

9. The detachable prosthodontic device (100) of claim 1, wherein the screw thread (230) of the screw rod (134) has a screw pitch ranging from 0.1 to 1.0 millimeter.

10. The detachable prosthodontic device (100) of claim 1, wherein the screw head (132) has a diameter ranging from 0.5 to 3.0 millimeters.

* * * * *